United States Patent [19]

Green et al.

[11] 4,184,127

[45] Jan. 15, 1980

[54] FREQUENCY STABILIZED LASER

[75] Inventors: Robert B. Green, Morgantown, W. Va.; Richard A. Keller, White Rock, N. Mex.; Gabriel G. Luther, Gaithersburg, Md.; Peter C. Schenk, Damascus, Md.; John C. Travis, Gaithersburg, Md.

[73] Assignee: The United States of America as represented by the Secretary of Commerce, Washington, D.C.

[21] Appl. No.: 960,193

[22] Filed: Nov. 13, 1978

Related U.S. Application Data

[62] Division of Ser. No. 809,334, Jun. 23, 1977, Pat. No. 4,148,586.

[51] Int. Cl.² .............................................. H01S 3/13
[52] U.S. Cl. ................................. 331/94.5 S; 356/308
[58] Field of Search ................... 331/94.5 S; 356/83

[56] References Cited

U.S. PATENT DOCUMENTS

| 3,691,478 | 9/1972 | Jacobs et al. | 331/94.5 S |
| 3,718,868 | 2/1973 | Pao et al. | 331/94.5 S |

Primary Examiner—William L. Sikes
Attorney, Agent, or Firm—Eugene J. Pawlikowski; Alvin J. Englert

[57] ABSTRACT

An apparatus and method for utilizing the opto-galvanic effect to perform spectroscopic or analytic investigations of atomic or molecular species. A sample of the substance to be analyzed is vaporized in an analytical flame, gas discharge tube, high temperature furnace or the like, and the vapor is irradiated with chopped or pulsed variable wavelength monochromatic light. The electrical resistance of the vapor is monitored as the frequency of the radiation is tuned through one or more electronic transition frequencies of the substance. The resistance spectrum resembles the optical absorption spectrum of the species in the vapor. The optogalvanic effect may also be used to frequency lock a laser to a transition frequency of a substance in a gas discharge cell.

1 Claim, 7 Drawing Figures

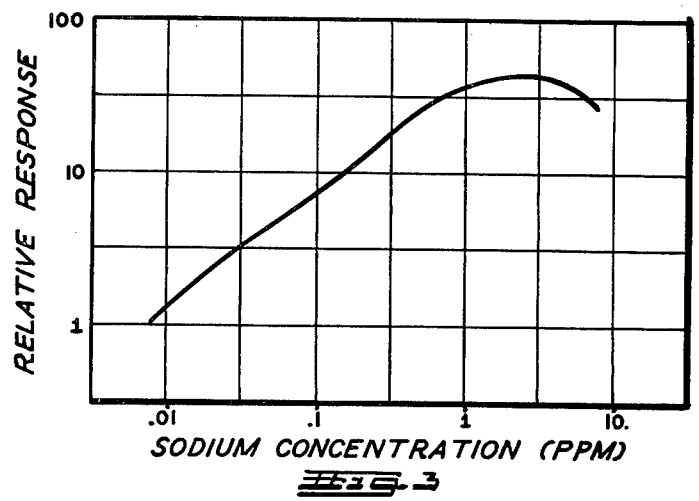
FIG. 3
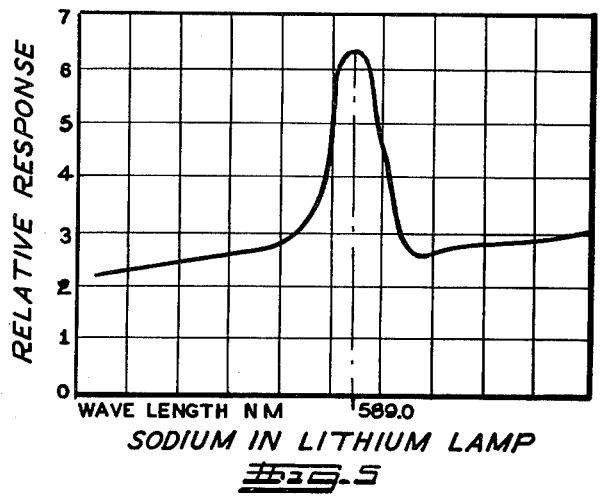
SODIUM IN LITHIUM LAMP
FIG. 5
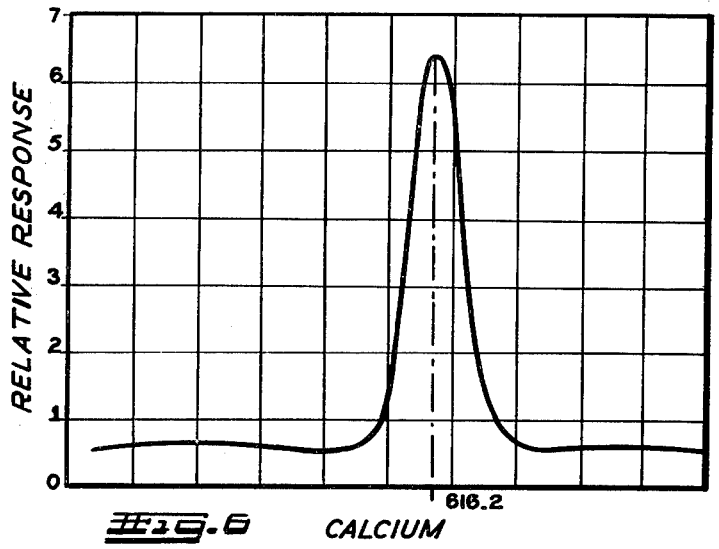
FIG. 6  CALCIUM

FREQUENCY STABILIZED LASER

This is a division of application Ser. No. 809,334 filed June 23, 1977 now U.S. Pat. No. 4,148,586.

The present invention relates to an improved apparatus and method for making spectroscopic and analytic determinations, and additionally for locking a laser to a predetermined frequency. In particular the present invention operates without requiring any optical detection and hence obviates the problems encountered by the prior art, which required such optical detection measurements.

While the techniques of optical spectroscopy, analytical chemistry, and flame analysis have been well developed over many decades, the methods utilized have typically been dependent upon the accurate measurement of an optical signal. This optical signal has often been weaker than desired, and the presence of scattered excitation and background light has caused significant signal to noise ratio problems, and has required that the collection efficiency of the process be closely controlled. Conversely, if the optical collection process has not been optimal, the sensitivity of the technique has been limited.

It is therefore an object of the invention to provide an apparatus and method for making spectroscopic, analytical, and flame diagnostic measurements independently of the measurement of an optical signal.

It is further an object of the invention to make such measurements with greater ease and/or sensitivity than has been done in the prior art.

It is still a further object of the invention to provide an opto-galvanic technique for frequency locking a laser to many more wavelengths than have been easily attainable before.

The above objects are accomplished according to the invention by providing an apparatus and method in which transitions in atomic or molecular species are indicated by a change in the electrical resistance (or conductance) rather than by a change in the optical absorption of the vaporized sample. The resistance is conveniently measured by placing two electrodes in the vapor and connecting the electrodes and a current limiting resistor across a constant voltage source. The voltage across the electrodes is then proportional to the resistance of the vapor, divided by the vapor resistance plus the current limiting resistance. If the current limiting resistance is very much larger than the vapor resistance, the voltage across the electrodes is substantially proportional solely to the vapor resistance. If the series resistance is much smaller than the vapor resistance, the current through the vapor is substantially proportional to the vapor conductance.

In the embodiments disclosed, the sample may be vaporized in a flame, a gas discharge tube, a high temperature furnace or the like. Two electrodes may be immersed in the vapor and a substantially constant current passed between them. The vapor is irradiated by intense monochromatic radiation and at a transition wavelength of the species, a change in the voltage across or current between the electrodes is detected. A spectral analysis of the species may be performed by varying the laser frequency and measuring the voltage or current change across the electrodes as a function of frequency. In the alternative, a chemical analysis may be performed by keeping the laser frequency constant at the transition frequency and measuring the voltage or current change, which corresponds in a predetermined way to the concentration of the species. Additionally, the laser may be effectively frequency locked to the transition frequency by feeding back a signal derived from the output signal at the electrodes.

The invention will be better understood by referring to drawings, in which:

FIG. 3 is a log-log graph of the relative opto-galvanic effect signal as a function of sodium concentration.

FIG. 5 is a graph of the opto-galvanic effect signal as a function of frequency obtained with the arrangement of FIG. 4, and shows the 589.0 nm line of sodium contamination in a lithium discharge lamp.

FIG. 6 is a graph showing the opto-galvanic effect signal as a function of frequency obtained with the arrangement of FIG. 4, and shows the 616.2 nm excited state transition of calcium in a discharge lamp.

Figure 1:
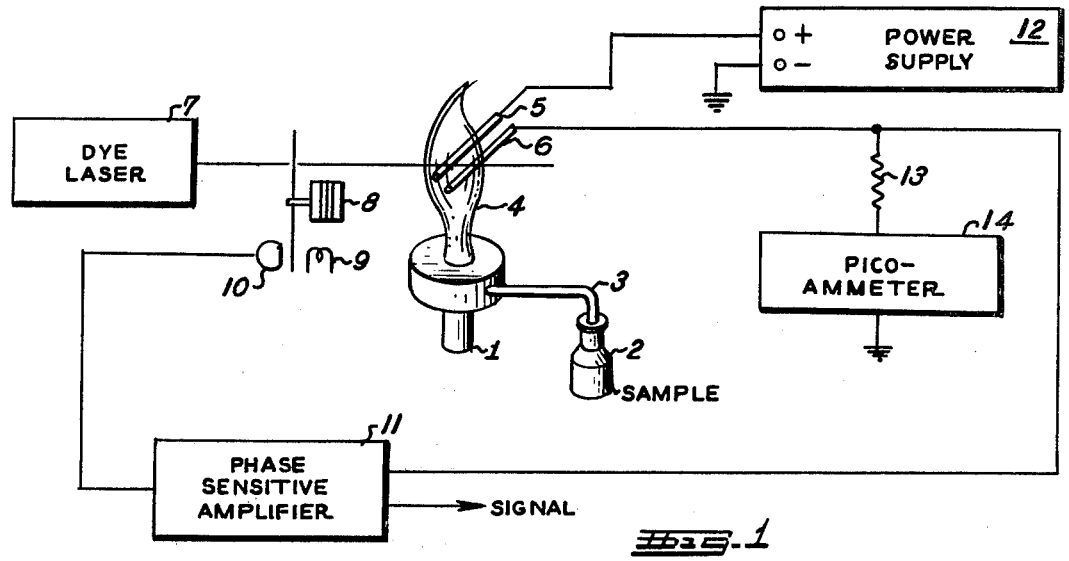
FIG. 1 is a block diagram of a first embodiment of the invention, in which the sample is vaporized in a flame.

Referring to FIG. 1, a first embodiment of the invention for measuring the properties of species in flames or hot gases is shown. Burner 1 is provided for supplying flame 4 and electrodes 5 and 6 are located a fixed distance apart and are immersed in flame 4. If desired, the metal burner 1 could be used as one of the electrodes. A sample holder 2 and tube 3 are provided for feeding the sample to be tested into flame 4. Alternatively, the species could be a naturally occurring constituent of the flame or of a hot gas from a furnace, internal combustion engine, or other combustion source.

A dc power supply 12, which may be a battery, is provided and its output is connected across electrodes 5 and 6 via a series resistor 13. Additionally, the output of laser 7 which may be a dye laser is directed at the flame 4. When the wavelength of the laser output is equal to a transition wavelengh of a species in the flame a change in the current takes place, and this is the opto-galvanic effect which is utilized by the present invention. The change in current has been observed to be as large as a few percent and may be detected by a picoammeter 14 or by a voltmeter (not shown) which measures the voltage across, and hence current through, resistor 13.

The opto-galvanic effect may be utilized in at least two ways according to the invention. First, to determine the spectroscopic characteristic of the species in the flame, the frequency output of the laser may be varied and the opto-galvanic effect response measured as a function of the varying wavelength, thereby providing the spectroscopic characteristic. As is known, a species may be identified by knowledge of its spectroscopic characteristic. Second, the opto-galvanic effect may be utilized to measure the concentration of a species which is present in the flame or hot gas. In this case, the frequency of the laser may be fixed to a transition frequency of the species, and the electrode signal output is a predetermined function of the concentration. Additionally, the system of FIG. 1 may be utilized to study the properties of flames themselves, as well as the properties of species in the flames.

The output of laser 7 is preferably chopped with chopper 8 to provide an ac output signal which is synchronous with a reference signal generated by light source 9 and photodetector 10 disposed on opposite sides of the chopper. The output of photodetector 10 is fed to phase sensitive amplifier 11 along with the ac signal across resistor 13. Phase sensitive amplifier 11 detects the signal on resistor 13 which is in phase with the output of photodetector 10. Hence the signal which is outputted from phase sensitive amplifier 11 has a relatively high signal to noise ratio.

In an actual apparatus which was built according to the teachings of the invention, burner 1 was a premix burner with a capillary burner head and was used with a fuel rich air-acetylene flame. The electrodes were tungsten welding rod, 1 mm in diameter and placed 4 mm apart. The flame was irradiated by a commercial, cw tunable dye laser chopper at 2 kHz. The bandwidth of the laser was approximatey 0.003 nm and the wavelength could be fine tuned over a range of 0.05 nm by tilting a 0.5 mm thick etalon located in the laser cavity. The laser power was approximately 50 mW.

Figure 2:
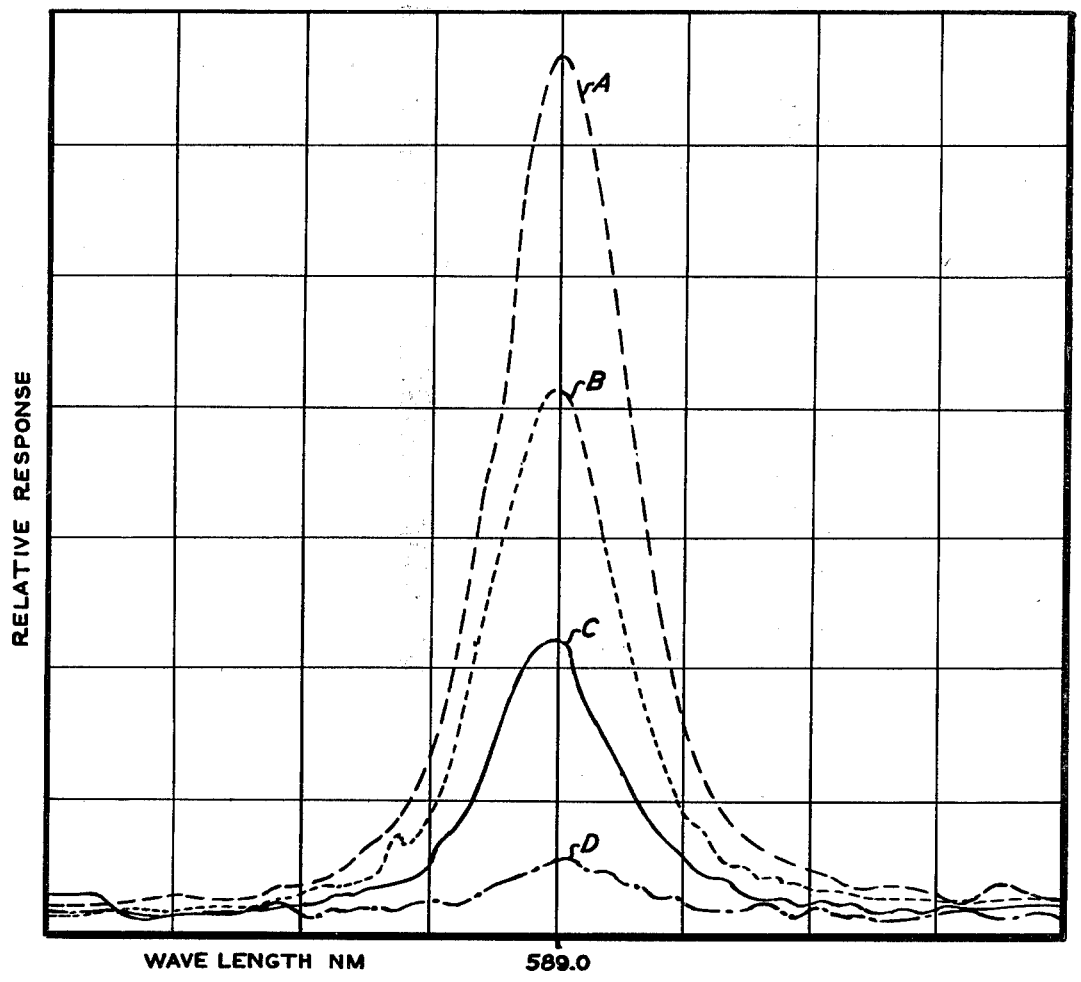
FIG. 2 is a graph of the opto-galvanic effect signal obtained as a function of frequency with the arrangement of FIG. 1 for several different concentrations of sodium.

In spectral and concentration tests performed on the element sodium, a sodium solution from sample holder 2 was aspirated into the flame 4. In the spectral test the ac signal output of phase sensitive amplifier 11 was displayed as a function of wavelength on a multichannel analyzer. The results are shown in the graph of FIG. 2 where lines A, B, C, and D correspond to concentrations of 10 ppb, 5 ppb, 2 ppb and 0, respectively. The signal to noise ratio for the 2 ppb data was greater than 20. Residual sodium contamination may be seen in the 0 concentration data.

FIG. 3 is a log-log graph of the output signal versus sodium concentration in parts per million. As indicated above, this data was obtained by adjusting the wavelength of the laser to be at the appropriate absorption wavelength for sodium. It is observed that the curve obtained is smooth and slightly less than linear before the onset of "self-reversal." Hence the apparatus shown in FIG. 1 may effectively be used to measure the concentration of a substance which is present in the flame or hot gas. The high sensitivity attained makes it possible to study species with low absorption cross sections and low fluorescence quantum yields or alternatively, species with appreciable absorption cross sections can be detected at very low concentrations.

Figure 4:
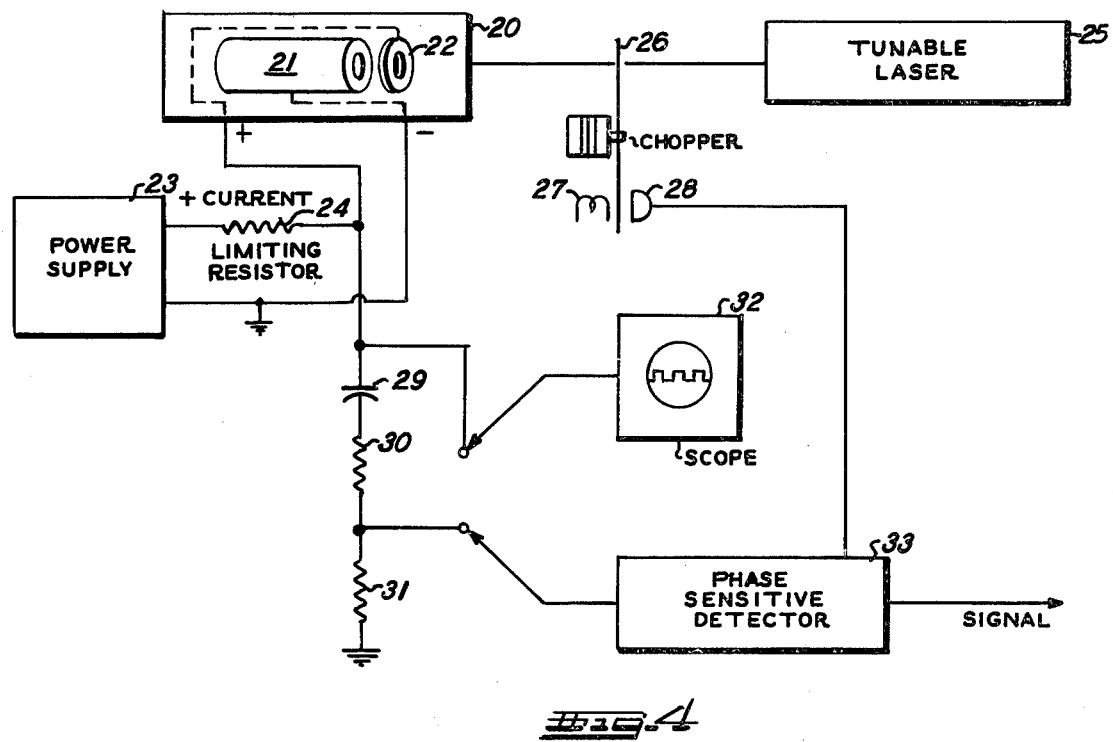
FIG. 4 is a block diagram of a second embodiment of the invention, which utilizes a gas discharge tube to vaporize the sample.

The embodiment shown in FIG. 4 utilizes the same concepts as that shown in FIG. 1, the difference being that the sample is vaporized in a discharge tube 20 instead of a flame. According to the arrangement shown in FIG. 4 spectral graphs of the substances in the discharge tube may be obtained and their concentrations may be determined. Since the components and methods used in the operation of the system of FIG. 4 are essentially the same as FIG. 1, these will not be repeated; however, it is noted that capacitor 29 not present in FIG. 1 is a dc isolating capacitor and oscilloscope 32 is provided for displaying the signal at the electrodes.

Discharge tube 20 may be any known such device, such as for instance, a hollow cathode atomic line source type tube. It is significant to note that excited state as well as resonance transitions may be detected. Further a discharge lamp may be designed to provide a reservoir of free atoms of a nonvolatile species sputtered from the cathode by buffer gas ions.

In actual measurements made on several low pressure gas discharge tubes, a cw dye laser was operated at a bandwidth of approximately 0.003 nm over a range of approximately 570 to 640 nm, with typical powers of 0.1 to 0.2 watts. The laser beam was mechanically chopped at a convenient rate such as 2 kHz and was directed through a 27 cm focal length lens into the discharge. With the tubes used, the anode voltage was approximately 120 volts and spectral scans of the line profiles were obtained by signal averaging the output of the lock-in amplifier for repetitive scans of the laser wavelength.

Several of the discharge tubes tested were commercial hollow cathode lamps having neon buffer gas and cathodes spiked with lithium, sodium, calcium, barium, mercury or uranium. The laser beam was usually directed along the lamp axis into the hollow cathode, but transverse illumination, avoiding both electrodes, also produced signals. Opto-galvanic effect signals were also observed from a cold cathode helium-neon discharge tube and a hot cathode helium-neon tube.

Signals corresponding to more than 30 neon transitions originating at excited electronic states could be observed with any of the discharge tubes in the 640 to 570 nm wavelength region. Some of these transitions resulted in a voltage change larger than three volts. The strongest signals originated from transitions from the metastable state of neon, 16.6 eV above the ground state.

Spectra were also obtained from transitions from the excited states of lithium, sodium, and calcium. FIG. 5 is a plot of the 589.0 nm transition of sodium in a lithium lamp which was obtained with the system of FIG. 4. Similarly, FIG. 6 is a plot of the 616.2 nm transition of calcium in a discharge lamp. In the plots of FIGS. 5 and 6, the total wavelength range depected is 0.05 nm.

According to a further embodiment of the invention, the opto-galvanic effect is utilized to frequency lock a laser to any characteristic transition frequency of a substance in discharge cell. The opto-galvanic technique is an improvement over the prior art because it obviates any problems encountered with scattered excitation light and, therefore, permits the use of weak transitions for frequency locking that otherwise would be inaccessible. Unlike in the prior art, large oscillator strengths and luminescence yields are not necessary.

Figure 7:
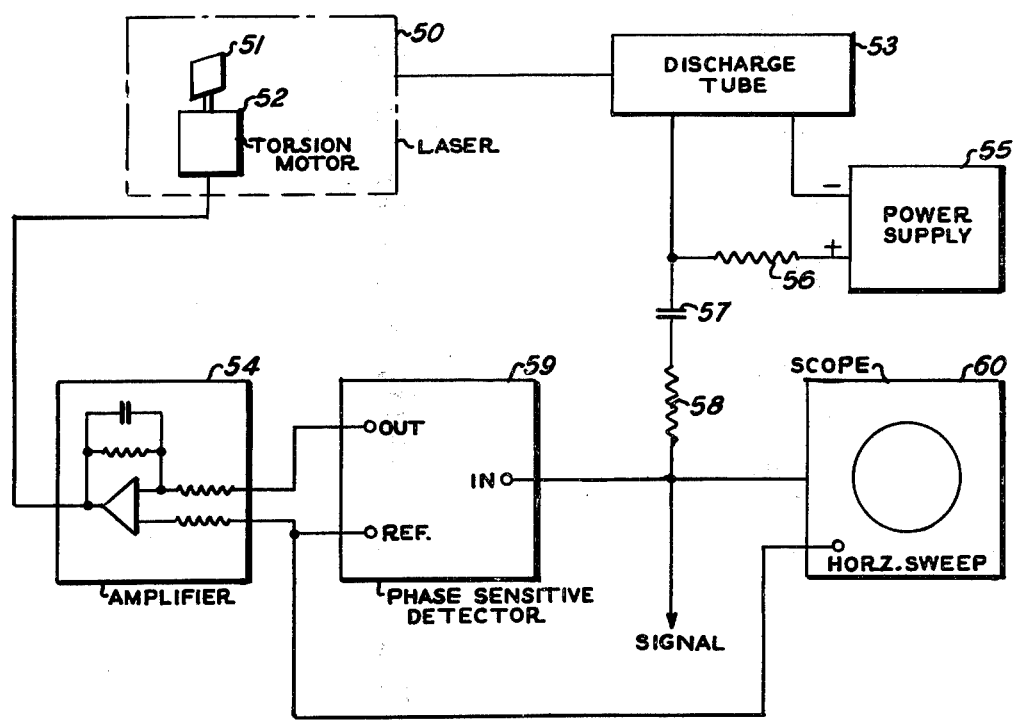
FIG. 7 is a block diagram of an embodiment of the invention which is utilized for locking a laser to a predetermined frequency.

A block diagram of the laser locking system of the invention is shown in FIG. 7. A laser 50 is arranged to irradiate a gas discharge tube 53 which is connected to a dc power supply 55 by a current limiting resistor 56. The output signal from the discharge tube 53 is coupled by a dc blocking capacitor 57 and a resistor 58 to an oscilloscope 60 and to the input of a phase sensitive detector 59. An ac reference signal (dither) from the phase sensitive detector 59 is used to frequency modulate the laser 50 in any convenient manner, for example, by oscillating a torsion motor 52 coupled to an etalon 51 in the laser 50. An operational amplifier 54 adds the ac reference signal to the dc output signal of the phase sensitive detector 59 and supplies the resultant signal to the torsion motor 52. If the center frequency of the modulated laser radiation equals the center frequency of a transition of a species in the discharge tube 53, the output signal from the discharge tube 53 will contain only second and higher harmonics of the reference signal from the phase sensitive detector 59 and the dc output of the phase sensitive detector 59 will be zero. However, if the center frequency of the modulated radiation differs from the transition center frequency, the output signal from the discharge tube 53 will contain the first harmonic of the ac reference signal, either in phase or 180° out of phase with the ac reference signal, thereby producing a dc error signal which will force the center position of the oscillating etalon 51 to shift so as to equalize the center frequencies of the modulated radiation and the transition. The frequency of laser 50 is thus locked to a characteristic transition frequency of the species in the discharge tube 53.

The frequency locking technique of the invention is applicable to many elements of the periodic table, and extends to transitions originating from excited states as well as the ground state. The ready availability of elemental hollow cathode lamps and the accessibility of excited state transitions and the improved results due to the fact that no optical signal need be measured favor the application of the opto-galvanic effect to laser stabilization.

It should be understood that while the above invention has been described with reference to atomic transitions in species it is contemplated that transitions corresponding to molecular species which are stable in an excitation environment may also result in observable signals. Similarly, it is contemplated that the lasers used in the various embodiments of the invention may comprise pulsed, as well as continuous, wave sources. It is further contemplated that the electrical resistance, conductance, etc. of the vapor may be monitored using microwaves and waveguides or cavities as an alternative to using electrodes and dc or low frequency ac currents. Further, while we have described illustrative embodiments of our invention, we wish it to be understood that we do not wish to be restricted solely thereto, but intend to cover all modifications thereof which would be apparent to one skilled in the art and which come within the spirit and scope of the claims appended hereto.

We claim:

1. A frequency stabilized laser comprising:
   an electrically tunable dye or other wide band laser which can be tuned to a selected narrow band of frequencies;
   a gas discharge tube arranged to be irradiated by said tunable laser, said discharge tube containing a substance having an electronic transition frequency to which said tunable laser is to be locked;
   means for dithering the tuning of said tunable laser;
   means for electrically exciting said gas discharge tube to provide an atomic or molecular vapor of said substance and also for providing a signal the amplitude of which is a function of the electrical resistance of said irradiated vapor and therefore of the instantaneous deviation of said dithered laser frequency from said transition frequency; and
   means responsive to said signal for maintaining the center of the dithered laser frequency at said transition frequency.

* * * * *